United States Patent
Fischer

(10) Patent No.: US 6,488,428 B1
(45) Date of Patent: Dec. 3, 2002

(54) FLUID ASSEMBLY CONTAINING A BREAKING COMPONENT FOR RELEASE OF FLUID AND METHOD THEREFORE

(75) Inventor: Gregory A. Fischer, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/781,538

(22) Filed: Feb. 8, 2001

(51) Int. Cl.⁷ .................................................. B43K 5/14
(52) U.S. Cl. ........................... 401/133; 401/134; 604/3; 604/20
(58) Field of Search .................. 401/132, 133, 401/134, 135; 222/80, 81, 83; 604/3, 20

(56) References Cited

U.S. PATENT DOCUMENTS

| | | | |
|---|---|---|---|
| 3,334,790 A | | 8/1967 | Eaton |
| 3,548,562 A | * | 12/1970 | Schwartzman ............... 222/80 |
| 3,635,567 A | | 1/1972 | Richardson, Jr. |
| 3,636,922 A | | 1/1972 | Ketner |
| 3,826,259 A | | 7/1974 | Bailey |
| 3,986,640 A | | 10/1976 | Redmond |
| 4,127,339 A | | 11/1978 | Malacheski |
| 4,140,409 A | | 2/1979 | DeVries |
| 4,258,863 A | * | 3/1981 | Ness ............................ 222/83 |
| 4,430,013 A | | 2/1984 | Kaufman |
| 4,493,574 A | | 1/1985 | Redmond et al. |
| 4,878,775 A | | 11/1989 | Norbury et al. |
| 4,902,154 A | * | 2/1990 | Valenza ..................... 401/132 |
| 5,098,297 A | | 3/1992 | Chari et al. |
| 5,288,289 A | * | 2/1994 | Haak et al. ................... 604/20 |
| 5,377,874 A | * | 1/1995 | Brown ......................... 222/82 |
| 5,538,353 A | | 7/1996 | DeHavilland |
| 5,628,729 A | | 5/1997 | Okabe |
| 5,645,527 A | * | 7/1997 | Beck ............................ 604/20 |
| 5,775,826 A | | 7/1998 | Miller |

* cited by examiner

Primary Examiner—David J. Walczak
(74) Attorney, Agent, or Firm—Factor & Partners

(57) ABSTRACT

A fluid assembly for a bioelectrode for use in a drug delivery device and a method for using such an assembly. The fluid assembly includes a reservoir for containing a fluid, and a barrier member for securing the fluid therein. The reservoir includes a breaking component positioned therewithin for breaking at least a portion of the barrier member upon application of a downward force to the reservoir. The breaking component is constructed from a material which is substantially chemically non-reactive relative to the fluid to be retained in the reservoir, the interior surface of the reservoir itself, and to at least that portion of the barrier member operatively in contact with the fluid.

33 Claims, 2 Drawing Sheets

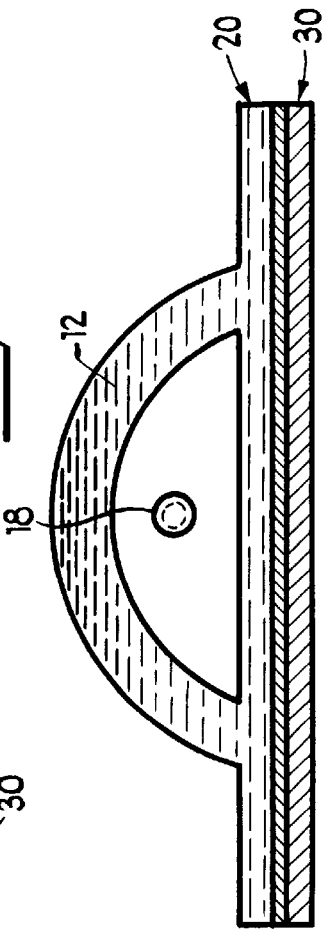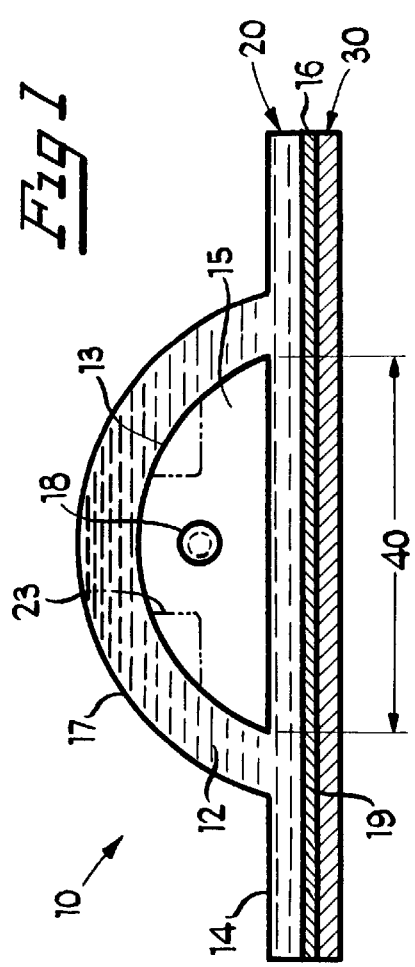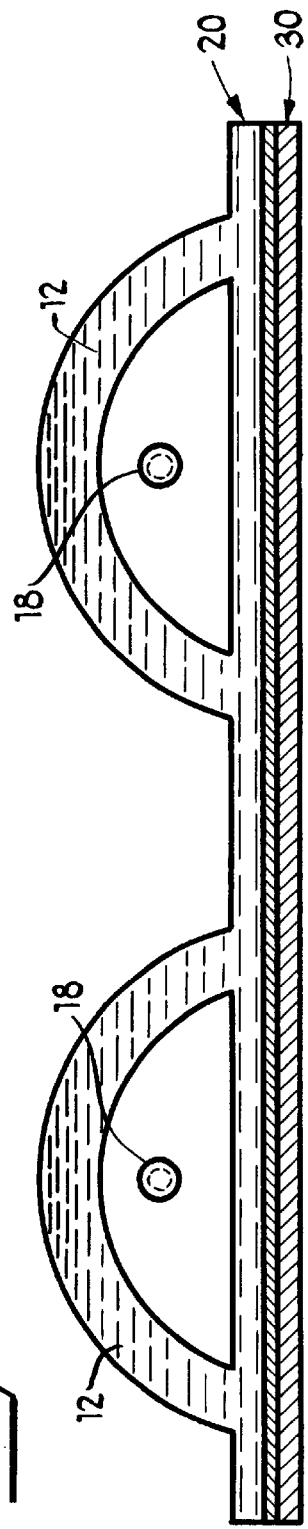

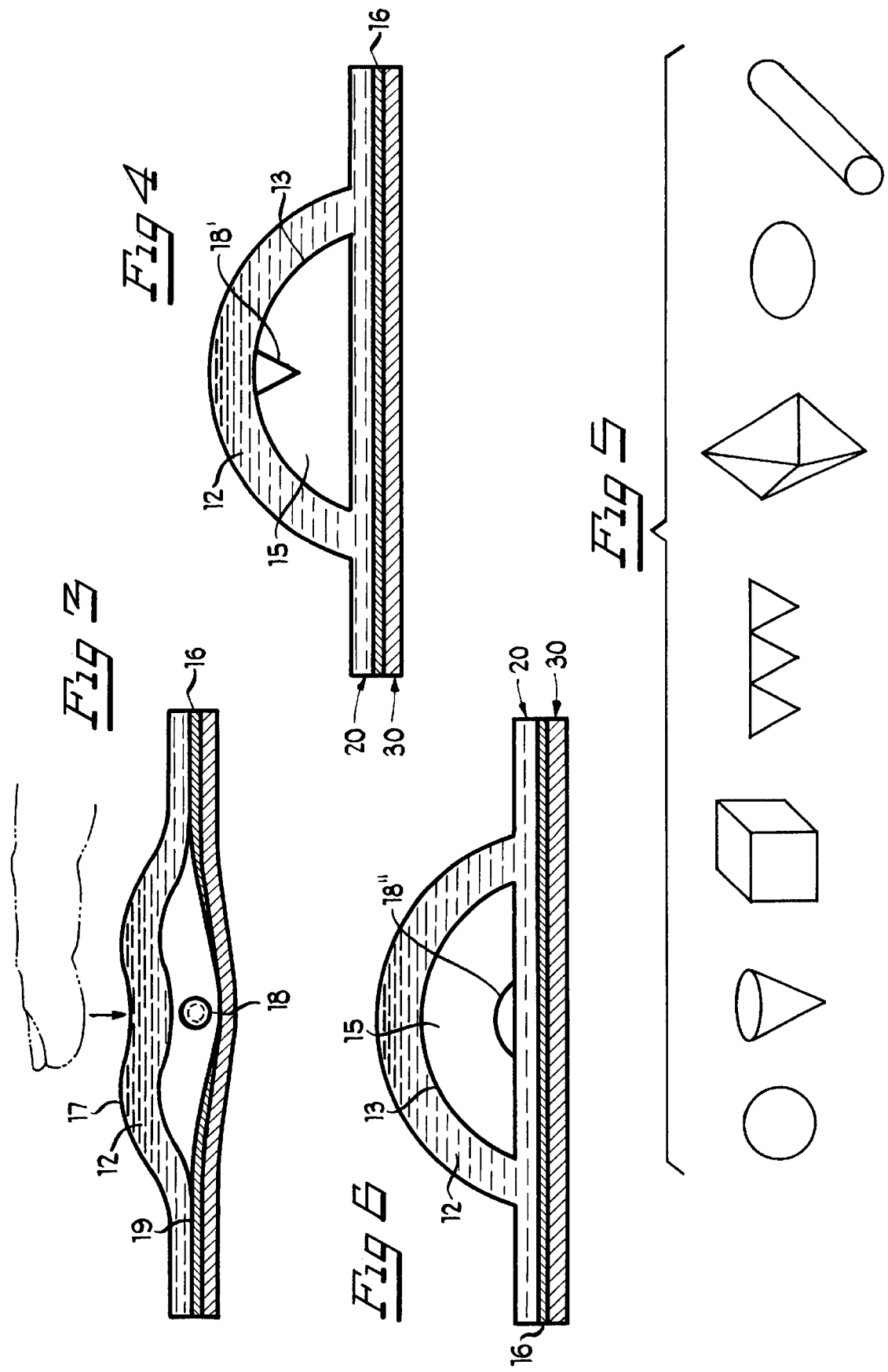

FLUID ASSEMBLY CONTAINING A BREAKING COMPONENT FOR RELEASE OF FLUID AND METHOD THEREFORE

BACKGROUND OF THE INVENTION

1. Field of the Invention

The present invention relates in general to drug delivery devices used to deliver ionic medicaments through the skin or other tissues, and, more particularly, to fluid delivery assemblies for delivering a fluid to a bioelectrode element.

2. Background Art

Drug delivery devices have been known in the art for several years. Furthermore, drug delivery devices having fluid delivery assemblies for delivering fluid to bioelectrodes are likewise well known and are the subject of many United States Patents including: U.S. Pat. No. 4,878,775; U.S. Pat. No. 4,493,574; and U.S. Pat. No. 5,817,044.

U.S. Pat. No. 4,878,775 discloses a fluid transfer device having a rigid portion, a chamber containing microcapsules of fluid, and a layer of permeable material. The microcapsules are ruptured by placing pressure upon the rigid portion, expelling the fluid through the permeable material and onto the surface of application.

U.S. Pat. No. 4,493,574 discloses a dispenser package having a fault line or cut pattern scored into a relatively stiff material, to which a pouch containing a fluid is attached. The ends of the stiff material are then formed into a "V" shape breaking the pouch and delivering the fluid through one or more holes pre-cut in the fault line.

U.S. Pat. No. 5,817,044 discloses an iontophoretic drug delivery device with an electrode reservoir and drug reservoir, where a liner separates the two components. The liner must be peeled or ripped away, allowing fluid to flow from the drug reservoir to the electrode reservoir.

SUMMARY OF THE INVENTION

The present invention is directed to a fluid assembly for a bioelectrode for use in a drug delivery device, comprising a reservoir, having an interior region, containing a fluid therein; a barrier member associated with the fluid reservoir for precluding inadvertent release or migration of the fluid out of the reservoir, and means for breaking at least a portion of the barrier so as to allow release of fluid from the fluid reservoir. The breaking means may comprise an inert component positioned within the interior region of the fluid reservoir.

In a preferred embodiment of the invention, the reservoir includes means for facilitating depression of at least a portion of the reservoir. In this embodiment, the reservoir has a bottom region juxtaposed with the barrier member, and a top region. The depression means is preferably integrally associated with the top region of the reservoir. However, it is also contemplated that such a depression means comprise an external, or internal component attached to, or near the top region of the reservoir. For example, an additional piece of material, such as plastic, can be associated therewith to further facilitate depression.

In another preferred embodiment, at least a portion of the reservoir has a tensile strength greater than the tensile strength of the barrier.

In a preferred embodiment of the invention, the breaking means is freely positioned within the interior region of the reservoir. In such an embodiment, the breaking means is selected from the group of geometries consisting of spherical, cubical, tetrahedronal, octahedronal, dodecahedronal, icosahedronal, cylindrical, conical, ellipsoidal, toothed, circular, oval, triangular, rectangular, square, or polygonal configurations.

It is further contemplated that the interior region of the reservoir include at least one position retainment member. In such an embodiment, the position retainment member serves to keep the breaking component within a confined area within the reservoir.

In still another preferred embodiment of the invention, the breaking means is attached with at least a portion of the reservoir. Preferably, the reservoir has a top region, and the breaking means is attached with the top region.

In yet another preferred embodiment of the invention, the breaking means is attached with the barrier member. In this, as well as the other preferred embodiments, the breaking means may have a hardness greater than that of barrier member.

The present invention is also directed to a method for releasing a fluid from a fluid assembly to a receiving member of a drug delivery device. The method preferably comprises the steps of: (a) applying a force to an external surface of a fluid reservoir of the fluid assembly; (b) depressing at least a portion of the fluid reservoir upon application of the force; (c) forcing a breaking component located within an interior region of the fluid reservoir, toward and into contact with a barrier member, wherein the barrier member serves to preclude inadvertent migration and release of fluid out of the fluid reservoir; (d) breaking at least a portion of the barrier member with the breaking component; and (e) releasing fluid from within the fluid reservoir, past the barrier member, and toward and into contact with a receiving member.

Although the described method alludes to forcing the breaking component toward the barrier, the present invention is also directed to associating the breaking component with the barrier member, and forcing at least a portion of the fluid reservoir towards that breaking component to, in turn, break at least a portion of the barrier member therewith.

BRIEF DESCRIPTION OF THE DRAWINGS

The invention will now be described with the reference to the following drawings, wherein:

FIG. 1 of the drawings is a perspective view of the present invention as attached with a drug delivery device;

FIGS. 2A and 2B of the drawings are cross-sectional views of a drug delivery device showing, among other things, the flexibility of associating one or more fluid assemblies with one or more receiving members;

FIG. 3 of the drawings is a cross-sectional view of a drug delivery device in operation;

FIG. 4 of the drawings is a cross-sectional view of an alternative embodiment of the drug delivery device of the present invention;

FIG. 5 of the drawings illustrates a number of possible geometric configurations for the construction of the breaking means; and FIG. 6 of the drawings is a cross-sectional view of an alternative embodiment of the drug delivery device of the present invention.

BEST MODE OF THE INVENTION

While this invention is susceptible of embodiment in many different forms, there is shown in the drawings and described herein several specific embodiments with the understanding that the present disclosure is to be considered as an exemplification of the principles of the invention and is not intended to limit the invention to the embodiments illustrated.

Drug delivery device 10 is shown in FIG. 1 as comprising fluid assembly 20, fluid receiving member 30, and conventional power source (not shown). Fluid assembly 20 includes reservoir 12, reservoir housing 14, and barrier member 16. Reservoir 12 includes interior surface 13 which defines interior region 15. In its intended environment, the interior region houses a fluid, such as a medicament or a hydrating fluid, for eventual dispersion upon receiving member 30. Dispersion of fluid will be aided, as discussed below, by the inclusion of breaking means 18 in interior region 15 of reservoir 12. As will be understood by those having ordinary skill in the art, the fluid receiving member may comprise a conventional dispersive iontophoretic electrode.

Reservoir 12 includes top region 17, bottom region 19, and means for facilitating depression therein. The depression facilitation means may be a function of the actual material of the reservoir, or, alternatively, and not shown, it may comprise a separate component associated with top region 17 of the reservoir 12. For example, when the depression facilitating means is part of the material (e.g. thin, flexible plastic), depression is accomplished upon exposure to a downward force applied thereto, such as by a thumb of an individual. As can be seen in FIG. 3, the depression enables breaking means 18 to contact and break at least a portion of barrier member 16, and, in turn, to release fluid from reservoir 12.

Although the depression facilitating means may be associated with reservoir 12 in any number of configurations, it is preferable to associate it with top region 17 of reservoir 12, so that when force is applied, depression proceeds in the direction of bottom region 19 and barrier member 16. It will also be appreciated that reservoir 12 will be constructed from material that is substantially impermeable to the fluid housed in interior region 15, while remaining substantially chemically inert to that same fluid as well as to barrier member 16. For example, reservoir 12 may be constructed from conventionally accepted materials, including, but not limited to, plastics, foils, polymers, and/or laminates designed to be compatable with the particular medicament used.

As shown in FIG. 1, barrier member 16 is operatively attached to bottom region 19 of reservoir housing 14. Such attachment may be by any number of conventional attachment methods, including adhesive, welding, etc. In addition, as can be seen, barrier member 16 must completely pass over the otherwise exposed area 40 of interior region of reservoir 12 so as to secure the fluid within reservoir 12.

Barrier member 16 is constructed from a conventional material that is substantially impermeable to the fluid to be retained within interior region 15 of reservoir 12. Such material can comprise, for example, plastics, foils, polymers and/or laminates designed to be compatable with the particular medicament used,. However, numerous other materials as would be readily understood to those having ordinary skill in the art can also be used, provided such materials are substantially chemically inert (at least where it comes into contact with the fluid and reservoir) relative to the particular fluid within reservoir 12 as well as with respect to the material of reservoir 12 itself.

Breaking means 18 is shown in FIGS. 1–3 as comprising a substantially chemically inert component (such as a ball or other configuration constructed from, among other materials, stainless steel, an inert plastic or polymer of sufficient hardness to penetrate barrier member 16), relative to the fluid within the reservoir, the reservoir itself, and at least that portion of barrier member 16 which the breaking member may come into contact with prior to breaking. As will be explained in greater detail, breaking means 18 can be freely positioned within the reservoir (as shown in FIG. 1), or, it can be attached to a portion of either interior surface 13 of the reservoir (as shown in FIG. 4), or to a portion of barrier member 16. Additionally, and as shown in dashed lines in FIG. 1, when the breaking means is freely positioned within the reservoir, at least one position retainment member 23 can be associated with the interior region of the reservoir. Such position retainment members serve to maintain the breaking means within a defined region within the reservoir so that the breaking means does not float out of an optimum location when actual breaking of the barrier member is desired.

As shown in FIG. 5, breaking means 18 can have any one of a number of geometries. However, it is important that the breaking means be formed from a material capable of piercing/breaking barrier member 16 (e.g. it is harder). Aside from that one requirement, breaking means 18 is capable of being formed in a variety of shapes, both three-dimensional and two-dimensional. For example, breaking means 18 may be spherical, cubical, tetrahedronal, octahedronal, dodecahedronal, icosahedronal, cylindrical, conical, ellipsoidal, toothed, circular, oval, triangular, rectangular, square, or polygonal in shape. This list is by no means exhaustive, as nearly any shape would be sufficient to provide a focus for the eventual application of force and subsequent breaking of the barrier member 16, described below.

As stated above, and as shown in FIG. 1, breaking means 18 is entirely encompassed in interior region 15 of reservoir 12. However, breaking means 18 may be freely placed within interior region 15 (as in FIG. 1), attached to either interior surface 13 of reservoir 12 (as shown as 18' in FIG. 4) or, to barrier member 16 (as shown as 18" in FIG. 6). When the breaking means is attached, for example, to interior surface 13 of the reservoir, such attachment may occur in any number of ways. For example, the breaking means may be integral to interior surface, creating an unbroken piece, or may be affixed to interior surface 13 by conventional means, such as adhesive or welding. Importantly, if breaking means 18' is attached, all parts of the exposed attachment process must be substantially chemically inert with respect to fluid in the interior region 15.

Similarly, and as shown in FIG. 6, breaking means 18" may be attached to barrier member 16. Again, barrier member 16 and breaking means 18" may be manufactured integrally, or, the breaking means may be attached later as a separate component, by, for example, adhesive or welding. Once attached, breaking means 18" serves as a focus for the application of force to the barrier member 16 (once a force is applied to reservoir 12 upon the forced depression of the fluid reservoir).

Various applications are contemplated for drug delivery device 10, depending on the desired application. However, the drug delivery device is preferably used with application of a medicament to a patient. For example, fluid assembly 20 may release an ionic medicament and/or an electrolyte solution into receiving member 30 for iontophoretic application. Depending upon the desired application and materials, several configurations of drug delivery device 10 are possible. For example, and as shown in FIG. 2A, if the fluid in the reservoir comprises a mixture of an ionic medicament and electrolyte, it is possible to pair a single fluid reservoir 12 with a single receiving member 30. As shown in FIG. 2B, if two or more fluids must be separately released into receiving member 30, two or more separate fluid reservoirs 12 may be paired with a single or corresponding number of receiving members 30.

Additionally, and as known in the prior art, it may be possible to create a chemical compound, such as for example a hydrate, using drug delivery device 10. First, receiving member 30 may be impregnated with at least a portion of the desired compound in a non-hydrated form. A hydrating fluid can then be positioned within fluid reservoir 12. When the fluid from within fluid reservoir 12 is released onto receiving member 30, the previously non-hydrated compound will become hydrated, and, ready for iontophoretic application.

In operation, fluid assembly 20, and, more particularly, reservoir 12, is loaded with a pre-determined amount of desired fluid. Such loading can be accomplished by any number of conventional means. The reservoir is then sealed by barrier member 16 so as to secure the fluid therein. Fluid assembly 20 is then placed next to receiving member 30, with barrier member 16 positioned adjacent thereto.

When ready for use, an operator, for example a doctor, would position the enire drug delivery device 10 on a surface, such as a table, with the receiving member adjacent the surface. The operator then applies force to depression facilitating means of top region 17 by, for example, the use of a thumb or finger (in the direction of the arrow, as shown in FIG. 3).

Once force is applied to top region 17 of reservoir 12, the depression facilitating means allows the top region of reservoir 12 to depress inward. The force of this depression drives the top region of the reservoir toward and into breaking means 18. As force is continually applied, the breaking means is forced toward and into barrier member 16, to, in turn, cause a break thereto. (Of course, if the breaking means is actually attached to the interior region of the fluid reservoir, then, as the reservoir is depressed, it will simultaneously force the breaking means toward and into contact with the barrier member). Once the barrier member is broken/fractured, the fluid loaded within interior region 15 of reservoir 12 is released therefrom toward and into contact with receiving member 30.

After fluid is received by the receiving member 30, and retained therein/on through absorption, adsorption, or other similar methods known to those in the art, fluid assembly 20 is removed from the receiving member by, for example, peeling them apart from each other. At that point, the fluid assembly is discarded and the receiving member is conventionally affixed to a patient for delivery of the fluid by standard iontophoretic means.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A fluid assembly for use in a drug delivery device, comprising:
   a reservoir, having an interior region, containing a fluid therein;
   a barrier member associated with the fluid reservoir for precluding inadvertent release or migration of the fluid out of the reservoir;
   means for breaking at least a portion of the barrier so as to allow release of fluid from the fluid reservoir, wherein the breaking means comprises a drug compatible compound positioned within the interior region of the fluid reservoir; and
   a bioelectrode adjacent the reservoir, wherein the bioelectrode comprises a receiving member capable of receiving and retaining the fluid released from the reservoir.

2. The fluid assembly of claim 1, wherein the reservoir includes means for facilitating depression of at least a portion of the reservoir.

3. The fluid assembly of claim 2, wherein the reservoir has a bottom region juxtaposed with the barrier member, and a top region,
   the reservoir depression means being associated with the top region of the reservoir.

4. The fluid assembly of claim 1, wherein at least a portion of the reservoir has a tensile strength greater than the tensile strength of the barrier.

5. The fluid assembly of claim 1, wherein the breaking means is freely positioned within the interior region of the reservoir.

6. The fluid assembly of claim 5, further including means for retaining the breaking means within a desired boundry within the interior region of the reservoir.

7. The fluid assembly of claim 5, wherein the breaking means is selected from the group of geometries consisting of spherical, cubical, tetrahedronal, octahedronal, dodecahedronal, icosahedronal, cylindrical, conical, ellipsoidal, toothed, circular, oval, triangular, rectangular, square, or polygonal configurations.

8. The fluid assembly of claim 1, wherein the breaking means is attached with at least a portion of the reservoir.

9. The fluid assembly of claim 8, wherein the reservoir has a top region, and the breaking means is attached with the top region.

10. The fluid assembly of claim 1, wherein the breaking means is attached with the barrier.

11. The fluid assembly of claim 1, wherein the breaking means has a hardness greater than the barrier member.

12. A fluid assembly for use in a drug delivery device, comprising:
    a reservoir, having an interior region, for containing a fluid therein, a bottom region, and a top region,
    means for facilitating depression of at least a portion of the reservoir, integrally associated with the top region of the reservoir;
    a barrier member, juxtaposed with the bottom region of the reservoir, for precluding inadvertent release or migration of the fluid out of the reservoir;
    means for breaking at least a portion of the barrier so as to allow release of fluid from the fluid reservoir,
    the breaking means comprises a drug compatible compound positioned within the interior region of the fluid reservoir; and
    a bioelectrode adjacent the reservoir, wherein the bioelectrode comprises a receiving member capable of receiving and retaining the fluid released from the reservoir.

13. The fluid assembly of claim 12, wherein at least a portion of the reservoir has a tensile strength greater than the tensile strength of the barrier.

14. The fluid assembly of claim 12, wherein the breaking means is freely positioned within the interior region of the reservoir.

15. The fluid assembly of claim 14, wherein the breaking means is selected from the group of geometries consisting of spherical, cubical, tetrahedronal, octahedronal, dodecahedronal, icosahedronal, cylindrical, conical, ellipsoidal, toothed, circular, oval, triangular, rectangular, square, or polygonal configurations.

16. The fluid assembly of claim 12, wherein the breaking means is associated with at least a portion of the reservoir.

17. The fluid assembly of claim 16, wherein the breaking means is associated with the top region.

18. The fluid assembly of claim 12, wherein the breaking means is associated with the barrier.

19. The fluid assembly of claim 12, wherein the breaking means has a hardness greater than the barrier member.

20. A fluid assembly for use in a drug delivery device, comprising:

a reservoir, having an interior region, containing a fluid therein;

a barrier member associated with the fluid reservoir for precluding inadvertent release or migration of the fluid out of the reservoir;

means for breaking at least a portion of the barrier so as to allow release of fluid from the fluid reservoir,
      the breaking means comprises a drug compatible compound positioned freely within the interior region of the fluid reservoir; and a bioelectrode adjacent the reservoir, wherein the bioelectrode comprises a receiving member capable of receiving and retaining the fluid released from the reservoir.

21. The fluid assembly of claim 20, wherein the reservoir includes means for facilitating depression of at least a portion of the reservoir.

22. The fluid assembly of claim 21, wherein the reservoir has a bottom region juxtaposed with the barrier member, and a top region, the reservoir depression means being associated with the top region of the reservoir.

23. The fluid assembly of claim 20, wherein at least a portion or the reservoir has a tensile strength greater than the tensile strength of the barrier.

24. The fluid assembly of claim 20, wherein the breaking means is selected from the group of geometries consisting of spherical, cubical, tetrahedronal, octahedronal, dodecahedronal, icosahedronal, cylindrical, conical, ellipsoidal, toothed, circular, oval, triangular, rectangular, square, or polygonal configurations.

25. The fluid assembly of claim 20, wherein the breaking means has a hardness greater than the barrier means.

26. A fluid assembly for use in a drug delivery device, comprising:

a reservoir, having an interior region, containing a fluid therein;

a barrier member associated with the fluid reservoir for precluding inadvertent release or migration of the fluid out of the reservoir;

means for breaking at least a portion of the barrier so as to allow release of fluid from the fluid reservoir,
      the breaking means comprises a drug compatible compound positioned within the interior region of the fluid reservoir, and attached with the reservoir; and a bioelectrode adjacent the reservoir, wherein the bioelectrode comprises a receiving member capable of receiving and retaining the fluid released from the reservoir.

27. The fluid assembly of claim 26, wherein the reservoir includes means for facilitating depression of at least a portion of the reservoir.

28. The fluid assembly of claim 26, wherein the reservoir has a bottom region juxtaposed with the barrier member, and a top region, the reservoir depression means being associated with the top region of the reservoir.

29. The fluid assembly of claim 26, wherein at least a portion or the reservoir has a tensile strength greater than the tensile strength of the barrier.

30. The fluid assembly of claim 26, wherein the breaking means is selected from the group of geometries consisting of spherical, cubical, tetrahedronal, octahedronal, dodecahedronal, icosahedronal, cylindrical, conical, ellipsoidal, toothed, circular, oval, triangular, rectangular, square, or polygonal configurations.

31. The fluid assembly of claim 26, wherein the breaking means has a hardness greater than the barrier means.

32. A method for releasing a fluid from a fluid assembly from a fluid assembly to a receiving member of a drug delivery device, wherein the method comprises the steps of:

applying a force to an external surface of a fluid reservoir of the fluid assembly;

depressing at least a portion of the fluid reservoir upon application of the force;

forcing a breaking component located within an interior region of the fluid reservoir, toward and into contact with a barrier member, wherein the barrier member serves to preclude inadvertent migration and release of fluid out of the fluid reservoir;

breaking at least a portion of the barrier member with the breaking component; and releasing fluid from within the fluid reservoir, past the barrier member, and toward and into contact with a receiving member, wherein the receiving member comprises a portion of a bioelectrode, and the receiving member retains the released fluid until needed for application to a patient via the bioelectrode.

33. A method for releasing a fluid from a fluid assembly from a fluid assembly to a receiving member of a drug delivery device, wherein the method comprises the steps of:

applying a force to an external surface of a fluid reservoir of the fluid assembly;

depressing at least a portion of the fluid reservoir upon application of the force;

forcing the reservoir into a drug compatible breaking component located within an interior region of the fluid reservoir, where the breaking component is attached with a barrier member, and, wherein the barrier member serves to preclude inadvertent migration and release of fluid out of the fluid reservoir;

breaking at least a portion of the barrier member with the breaking component; and releasing fluid from within the fluid reservoir, past the barrier member, and toward and into contact with a receiving member, wherein the receiving member comprises a portion of a bioelectrode, and the receiving member retains the released fluid until needed for application to a patient via the bioelectrode.

* * * * *